United States Patent
Livak et al.

[11] 3,973,039
[45] Aug. 3, 1976

[54] [(2-ALKOXYBENZYLIDINE)AMINO]-GUANIDINES AND THEIR ANTICOCCIDIAL USE

[75] Inventors: John E. Livak, Rutland, Vt.; Paul B. Budde, Midland, Mich.

[73] Assignee: The Dow Chemical Company, Midland, Mich.

[22] Filed: Feb. 3, 1975

[21] Appl. No.: 546,850

[52] U.S. Cl. .............................. 424/326; 260/564 F; 260/562 H; 260/501.14; 424/316; 424/324
[51] Int. Cl.² ................ C07C 133/12; A61K 31/155
[58] Field of Search ....... 260/564 F, 562 H, 501.14; 424/324, 316, 326

[56] References Cited
UNITED STATES PATENTS

| | | | |
|---|---|---|---|
| 3,577,553 | 5/1971 | Ferlauto | 424/269 |
| 3,624,214 | 11/1971 | Stevenson | 424/326 |
| 3,769,432 | 10/1973 | Tomcufcik | 424/326 |

OTHER PUBLICATIONS

German Offenlegungsschrift 2,104,346 (1972) Hoechst.
German Offenlegungsschrift 2,104,347 (1972) Hoechst.
Science, vol. 168 pp. 373–374 (1970).

*Primary Examiner*—Gerald A. Schwartz
*Attorney, Agent, or Firm*—S. Preston Jones; C. Kenneth Bjork

[57] ABSTRACT

[(2-Alkoxybenzylidine)amino]guanidines and their pharmacologically acceptable salts are prepared and employed as anticoccidials. The compounds correspond to the formula

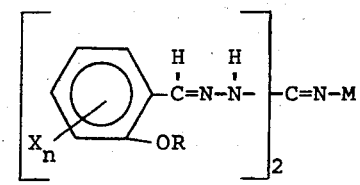

wherein R represents methyl, ethyl or benzyl; X represents chloro, bromo, amino, dimethylamino, diethylamino or acetamido; M represents hydrogen or the radical

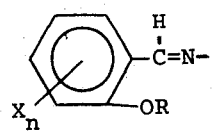

and $n$ represents an integer of 1 or 2 with the proviso that when $n$ is 1, the X representation is in the 4 ring position and when $n$ is 2, the X representations are in any of the 3, 4 or 5 ring positions.

18 Claims, No Drawings

# [(2-ALKOXYBENZYLIDINE)AMINO]GUANIDINES AND THEIR ANTICOCCIDIAL USE

BACKGROUND OF THE INVENTION

This invention relates to animal husbandry and more particularly to methods and compositions adapted to be employed to allow maximum normal growth of animals, for controlling protozoan organisms and for mitigating against the attack of gastrointestinal parasites. The term "animal" as used herein is employed in context of its general definition and is meant to include fowl, particularly domesticated fowl; i.e. poultry.

It is an object of the present invention to provide a new and improved practice for raising and benefiting animals such as rabbits, lambs, calves, chickens, guinea fowl, pigeons, geese, turkeys and other domesticated animals and to provide a new and improved method and composition for mitigating against and protecting animals from the attack of gastrointestinal parasites. Still another object is to provide a method and composition which may be employed prophylactically to protect animals from the attack of gastrointestinal parasites without adversely affecting the normal physiological processes.

SUMMARY OF THE INVENTION

The present invention is directed to [(2-alkoxybenzylidine)amino]guanidines and their pharmacologically acceptable salts and to the use of these compounds as anticoccidial agents. The guanidine compounds of the present invention correspond to the formula:

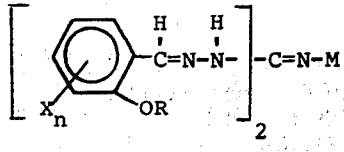

wherein R represents methyl, ethyl or benzyl; X represents chloro, bromo, amino, dimethylamino, diethylamino or acetamido; M represents hydrogen or the radical

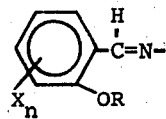

and $n$ represents an integer of 1 or 2 with the proviso that when $n$ is 1, the X representation is in the 4 ring position and when $n$ is 2, the X representations are in any of the 3, 4 or 5 ring positions.

The guanidine-type compounds are crystalline solids and are adapted to be administered to animals. The compounds are not repellent to animals and can be employed in admixture with grain rations, animal feeds or drinking water. They can be administered continuously or intermittently in dosages sufficient to allow maximum normal growth and utilization of feed and to protect the animal from the attack of gastrointestinal parasites without adversely affecting the normal physiological processes, or without imparting any unpalatable characteristic to animal flesh.

The compounds of the present invention are prepared by contacting an appropriate substituted 2-alkoxybenzaldehyde with a diamino- or -triaminoguanidine (depending upon whether a bis- or a -tris product is desired) in the presence of a solvent or reaction medium.

In carrying out the reaction, the guanidine reactant, as the bromide, chloride, sulfate or nitrate salt and the benzaldehyde reactant are contacted together, in the reaction medium and in the presence of an acidifying amount of a mineral acid, wherein the anion is the same as that set forth directly hereinbefore for the guanidine salt, at a temperature of from about room temperature up to the reflux temperature of the mixture for a period of from about 5 minutes to about 24 hours or more. The specific temperature employed is not critical, however, the use of higher temperatures such as reflux conditions favor a more rapid reaction rate.

At the completion of the reaction, the reaction mixture is cooled and the desired product recovered by filtration or other conventional separatory procedure. The product, if desired, can be purified by recrystallization from a solvent such as, for example, water, methanol, ethanol or mixtures thereof.

If it is desired that the product be in the form of the free base, the salt can be converted to the free base by conventional procedures such as by basifying the product. Such conversion is easily accomplished by treating the product with a base such as ammonium hydroxide, sodium hydroxide or other conventionally employed bases.

If it is desired that the product be present in the form of a different acid salt, such can be accomplished by conventional procedures such as by acidifying the free base compound with the desired pharmacologically acceptable acid.

Representative pharmacologically acceptable acid addition salt forms of the compounds include, the chloride, bromide, sulfate, nitrate, phosphate, acetate, citrate, 3-hydroxy-2-naphthalenecarboxylic acid and other conventionally employed pharmacologically acceptable acid addition salts.

Representative reaction mediums, i.e. solvents for carrying out the reaction include, for example, water, ethanol, aqueous ethanol, dimethylformamide or other conventional water-miscible organic solvents.

DESCRIPTION OF SOME PREFERRED EMBODIMENTS

The following examples illustrate the present invention and the manner by which it can be practiced but, as such, should not be construed as limitations upon the overall scope of the same.

EXAMPLE 1

1,2,3-Tris [((4-diethylamino)-2-ethoxybenzylidene)amino]-guanidine

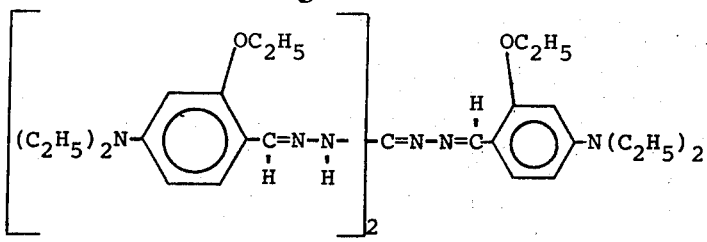

To a reaction flask was added 1.26 grams (0.009 mole) of trisaminoguanidine, hydrochloride, 1.0 milliliter of concentrated hydrochloric acid and 25 milliliters of a 50:50 mixture of water and ethanol. To this mixture was added 6 grams (0.025 moles) of 2-ethoxy-4-diethylaminobenzaldehyde and the mixture stirred at room temperature overnight. The mixture was filtered, and the recovered solid material was washed with 25 milliliters of 2B-ethanol and dried. The filtrate was concentrated by heating and the recovered solids recombined therewith. After further concentration the mixture was extracted with 50 milliliters of hot benzene followed by 75 milliliters of hot 2B-ethanol. The ethanolic extract was evaporated to a gummy residue which was mixed with 100 milliliters of deionized water and made basic by the addition of 25 milliliters of concentrated ammonium hydroxide. The crystals which formed were recovered by filtration, taken up in benzene and recrystallized therefrom by the addition of cyclohexane. The 1,2,3-tris[((4-diethylamino)-2-ethoxybenzylidene)amino]-guanidine product was recovered by filtration and dried and recrystallized from cyclohexane. The product was recovered in a yield of 5.7 grams (79 percent of theoretical) and melted at 106°–115°C. Upon analysis, the product was found to have carbon, hydrogen and nitrogen contents of 63.69, 8.33 and 17.21 percent, respectively, as compared with the theoretical contents of 67.30, 8.47 and 16.55 percent, respectively, calculated for the above-named structure.

EXAMPLE II 1,3-Bis[((4-diethylamino)-2-ethoxybenzylidene)amino]guanidine

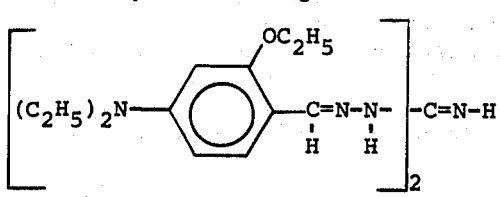

To a reaction flask was added 1.7 grams (0.0125 mole) of N,N-diaminoguanidine, hydrochloride, 1.0 milliliter of concentrated hydrochloric acid and 25 milliliters of a 50:50 mixture of water and ethanol. To this mixture was added 6 grams (0.025 mole) of 2-ethoxy-4-diethylaminobenzaldehyde and the mixture stirred at room temperature overnight. The mixture was filtered, and the recovered solid material was washed with 25 milliliters of 2B-ethanol and dried. The filtrate was concentrated by heating and the recovered solids recombined therewith. After further concentration the mixture was extracted with 50 milliliters of hot benzene followed by 75 milliliters of hot 2B-ethanol. The ethanolic extract was evaporated to a gummy residue which was mixed with 100 milliliters of deionized water and made basic by the addition of 25 milliliters of concentrated ammonium hydroxide. The crystals which formed were recovered by filtration, taken up in benzene and recrystallized therefrom by the addition of cyclohexane. The 1,3-bis[((4-diethylamino)-2-ethoxybenzylidene)amino]-guanidine product was recovered by filtration and dried and recrystallized from cyclohexane. The product was recovered in a yield of 6.4 grams and melted at 111°–127°C. Upon analysis, the product was found to have carbon, hydrogen and nitrogen contents of 61.27, 8.10 and 17.66 percent, respectively, as compared with the theoretical contents of 65.25, 8.32 and 19.82 percent, respectively, calculated for the above-named structure.

EXAMPLE III 1,3-Bis[(3,5-dibromo-2-benzyloxybenzylidene)amino]guanidine:hydrochloride

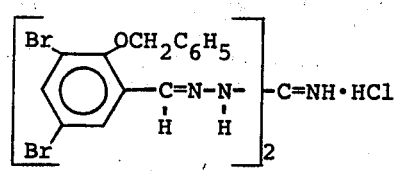

To a mixture of 2.1 grams (0.015 mole) of N,N'-diaminoguanidine, hydrochloride in 50 milliliters of 2B-ethanol and 2.0 milliliters of concentrated hydrochloric acid was added 11.1 grams (0.03 mole) of 2-benzyloxy-3,5-dibromobenzaldehyde. The mixture was stirred and heated to reflux temperature and maintained at this temperature overnight. At the completion of the reaction, the insoluble crystals contained in the reaction mixture were removed by filtration and dried under reduced pressure. The solid crude, 1,3-bis[((3,5-dibromo-2-benzyloxybenzylidene)-amino]guanidine, hydrochloride product was mixed with 250 milliliters of benzene refluxed, recovered by filtration and dried. The product was obtained in a yield of 11.3 grams and melted at 217°–218°C. Upon analysis, the product was found to have carbon, hydrogen and nitrogen contents of 41.83, 3.00 and 8.48 percent, respectively, as compared with the theoretical contents of 41.98, 2.92 and 8.44 percent, respectively, calculated for the above-named structure.

EXAMPLE IV 1,3-Bis[(3,5-dibromo-2-methoxybenzylidene)-amino]-quanidine:hydrochloride

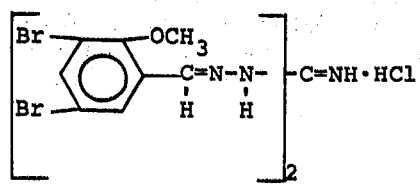

A mixture was prepared by dissolving 12.55 grams (0.1 mole) of diaminoguanidine, hydrochloride in 80 milliliters of lukewarm water and this mixture was added to a solution of 58.8 grams (0.2 mole) of 3,5-dibromo-2-methoxybenzaldehyde dissolved in 500 milliliters of ethyl alcohol at 60°C. To this mixture was added a solution of 10 milliliters of 37 percent hydrochloric acid in 100 milliliters of ethyl alcohol. The mixture was heated to reflux (86°C) for 10 minutes and thereafter cooled to 20°C. The solid 1,3-Bis[(3,5-dibromo-2-methoxybenzylidene)amino]guanidine hydrochloride product was recovered by filtration under reduced pressure, washed with ethanol and dried. The product was recovered in a yield of 47 grams (69.5 percent of theoretical) and melted at 203°–205°C. with decomposition.

EXAMPLE V 1,3-Bis[(3,5-dibromo-2-ethoxybenzylidene)amino]-guanidine:hydrochloride

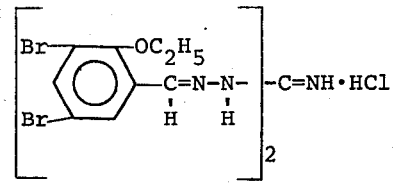

A mixture was prepared by dissolving 7.9 grams (0.063 mole) of diaminoguanidine, hydrochloride in 60 milliliters of lukewarm water and this mixture was added to a solution of 38.2 grams (0.125 mole) of 3,5-dibromo-2-ethoxybenzaldehyde dissolved in 500 milliliters of ethanol. To this mixture was added a solution of 8 milliliters of concentrated hydrochloric acid in 80 milliliters of ethanol. The mixture was heated at the reflux temperature for 10 minutes and thereafter cooled to 20°C. The solid 1,3-bis[(3,5-dibromo-2-ethoxybenzylidene)amino]guanidine, hydrochloride product was recovered by filtration under reduced pressure, washed with ethanol and dried. The product was recovered in a yield of 20 grams (45 percent of theoretical) and melted at 188°–190°C.

EXAMPLE VI 1,3-Bis[(4-acetamido-2-ethoxybenzylidene)-amino]-guanidine

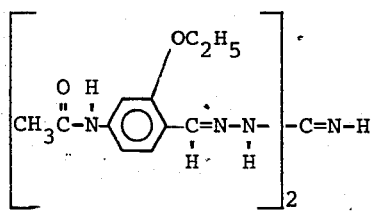

A mixture was prepared by dissolving 0.38 grams (0.003 mole) of diaminoguanidine, hydrochloride in 10 milliliters of warm water and this mixture was added to a solution of 1.04 grams (0.005 mole) of 4-acetamido-2-ethoxybenzaldehyde dissolved in 50 milliliters of ethanol. To this mixture was added 5 drops of 5 Normal (N) nitric acid. The mixture was heated at reflux (81°C.) for 2 minutes and 20 milliliters of 5 percent ammonium hydroxide was added thereto. The solid product which precipitated was recovered by filtration, washed with ethanol and dried. The 1,3-bis[(4-acetamido-2-ethoxybenzylidene)amino]guanidine product was recovered in a yield of 1.0 gram (71 percent of theoretical) and melted at 238°–240°C. with decomposition.

EXAMPLE VII 1,2,3-Tris[(4-acetamido-2-ethoxybenzylidene)-amino]guanidine:hydrochloride

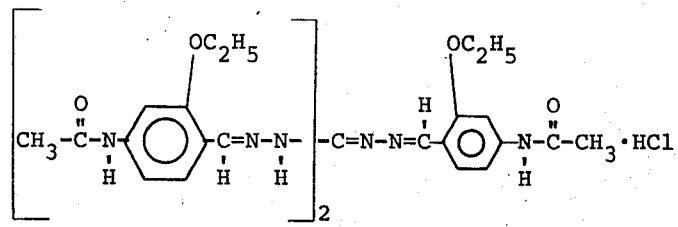

A mixture was prepared by dissolving 0.56 gram (0.004 mole) of triaminoguanidine, hydrochloride in 10 milliliters of warm water and this mixture was added to a solution of 2.07 grams (0.01 mole) of 4-acetamido-2ethoxybenzaldehyde dissolved in 50 milliliters of warm ethanol. To this mixture was added 1 milliliter of 5N hydrochloric acid and the mixture heated at the reflux temperature for 15 minutes. The solid 1,2,3-tris[(4-acetamido-2-ethoxybenzylidene)amino]guanidine, hydrochloride product which precipitated was recovered by filtration and washed with ethanol and dried. The product was removed in a yield of 0.6 grams (21 percent of theoretical) and melted at 170°–180°C. with decomposition.

The following compounds of the present invention are prepared in accordance with the methods hereinbefore set forth employing the appropriate starting reactants.

1,3-Bis[(4-amino-2-methoxybenzylidene)amino]-guanidine: hydrochloride, melting at 220°–230°C. with decomposition;

1,3-Bis[(4-acetamido-2-methoxybenzylidene)amino]guanidine:hydrochloride, melting at 287°–288°C. with decomposition;

1,3-Bis[(4-amino-2-ethoxybenzylidene)amino]-guanidine:hydrochloride, melting at 230°–235°C. with decomposition;

1,3-Bis[(4-(dimethylamino)-2-ethoxybenzylidene)amino]-guanidine, melting at 275°–280°C. with decomposition;

1,3-Bis[(4-bromo-2-ethoxybenzylidene)amino]-guanidine: hydrochloride, melting at 195°–197°C.;

1,3-Bis[(4-bromo-2-methoxybenzylidene)amino]-guanidine: hydrobromide, melting at 266°–267°C.;

1,3-Bis[(4-(and 5)-chloro-2-methoxybenzylidene)amino]-guanidine:hydrobromide, melting at 265°–266°C.;

1,3-Bis[(3,4-(and 4,5)-dichloro-2-ethoxybenzylidene)-amino]guanidine:hydrobromide, melting at 248°–250°C.;

1,3-Bis[(2-methoxy-4-nitrobenzylidene)amino]-guanidine: hydrochloride, melting at 236°–238° C., with decomposition;

1,3-Bis[(3,5-dichloro-2-methoxybenzylidene)amino]-guanidine:hydrochloride, melting at 233°–234°C., with decomposition;

1,3-Bis[(4-(and 5)-chloro-2-ethoxybenzylidene)amino]-guanidine:hydrobromide, melting at 214°–216°C.;

1,3-Bis[(4-bromo-2-methoxybenzylidene)amino]-guanidine:hydrochloride, melting at 257°–258°C, with decomposition;

1,3-Bis[(4,5-dichloro-2-ethoxybenzylidene)amino]-guanidine:hydrochloride, melting at 260°–261°C., with decomposition;

1,3-Bis[(4,5-dibromo-2-methoxybenzylidene)amino]-guanidine:hydrochloride, melting at 265°–267°C.;

1,3-Bis[(4,5-dichloro-2-methoxybenzylidene)amino]-guanidine:hydrochloride, melting at 272°–273°C., with decomposition;

1,3-Bis[(3,5-dibromo-2-methoxybenzylidene)amino]-guanidine, melting at 201°–203°C.;

1,3-Bis[(3,5-dibromo-2-methoxybenzylidene)amino]-guanidine:3-hydroxy-2-naphthalenecarboxylic acid; melting at 237°–239°C.;

1,3-Bis[(4-chloro-2-ethoxybenzylidene)amino]-guanidine:hydrochloride, melting at 180°–182°C.;

1,3-Bis[(4-acetamido-2-ethoxybenzylidene)amino]-guanidine:hydrochloride, melting at 255°–260°C., with decomposition;

1,2,3-Tris[(4-amino-2-methoxybenzylidene)amino]-guanidine:hydrochloride, melting at 240°–245°C., with decomposition;

1,2,3-Tris[(4-acetamido-2-methoxybenzylidene)amino]-guanidine:hydrochloride, melting at 220°–230°C., with decomposition;

1,2,3-Tris[(4-amino-2-ethoxybenzylidene)amino]-guanidine:hydrochloride, melting at 217°–220°C., with decomposition;

1,2,3-Tris[(2-methoxy-4-nitrobenzylidene)amino]-guanidine:hydrochloride, melting at 215°–220°C., with decomposition; and 1,2,3-Tris[(3,5-dichloro-2-methoxybenzylidene)amino]-guanidine:hydrochloride, melting at 198°–200°C., with decomposition.

The present invention also comprises a novel composition containing the guanidine compounds of the present invention as the active agent therein and a method for orally administering to animals the said guanidine compounds.

The practice of the method of the present invention allows maximum normal growth of the animals and protects the animals from parasitic diseases of the gastrointestinal tract and particularly from coccidiosis. Further, the practice protects the animals from mixed coccidial infections and from the various strains of the same species of coccidial organism and particularly from the various strains of Eimeria, tenella, Eimeria necatrix, Eimeria acervulina, Eimeria maxima and Eimeria brunetti. Also, while protecting the animals from coccidiosis, the practice allows the protected animals which are exposed to the coccidial infection to develop acquired immunity to the disease.

The oral administration of an effective dosage of the compounds of the present invention is essential and critical for the practice of the present invention. In general, good results are obtained when the animals are fed a daily dosage of from about three to about 1,000 parts of the compounds per million parts of dietary intake, and preferably from about 15 to about 250 parts per million parts of dietary intake. Where danger of reexposure to the attack of intestinal parasites from contaminated feed or surroundings is low, good results are obtained when the animals are fed a daily dosage of about 60 parts or more per million parts of dietary intake. By the term "dietary intake" is meant grain rations, animal feeds and/or drinking water.

The method of the present invention can be carried out by the oral administration of the unmodified compounds. However, the present invention also embraces the employment of a liquid, powder, mash, pellet, capsule or other animal food containing said compounds. In such usage, the compounds can be modified with one or more of a plurality of additaments including water, ethanol, skim milk, edible oils, propylene gylcol, syrups, grain rations, surface active dispersing agents such as the liquid and solid emulsifying agents and solid carriers such as edible powders and commercial animal feeds, concentrates or supplements. By "commercial animal feeds, concentrates or supplements" are meant the partial and complete animal feeds containing desirable amounts of minerals, vitamins, antioxidants, antibiotics and growth stimulants. Further, the compositions are adapted to be fed to animals to supply the desired dosage of active agents, or to be employed as concentrates and subsequently diluted with additional carrier to produce the ultimate compositions.

The exact concentration of the compounds to be employed in the compositions can vary provided that enough of the composition is ingested by the animal so as to provide the required internal amount of active ingredient as set forth hereinbefore. For example, where direct administration to the individual animal is preferred, liquid or solid compositions containing from 5 to 98 percent by weight of the agents conveniently are employed to supply the desired dosage. Where the compounds are provided as a constituent of the principal food ration, satisfactory results are obtained with food rations containing a minor but effective amount of the compounds. The exact amounts of the compounds in the ration are dependent upon the food consumption and feeding habits of the animal concerned. With most animals, the required dosage can be supplied with mash compositions containing from 0.001 to 0.1 percent by weight of active material when fed as the principal food ration. The compounds can also be furnished in the drinking water by conventional formulation techniques.

In liquid compositions to be employed as concentrates, the active agents can be present in a concentration of from 5 to 98 percent by weight. Preferred concentrate compositions oftentimes contain two or more percent by weight of a liquid or solid surface active agent.

Liquid compositions containing the desired amount of the compounds can be prepared by dissolving the compounds in ethanol, propylene glycol or an oil by dispersing them in water with or without the aid of a suitable surface active dispersing agent such as an ionic or non-ionic surface active agent. Suitable surface active dispersing agents include the glycerol and sorbitan esters of fatty acids and the polyoxyalkylene derivatives of fatty alcohols and of sorbitan esters. The aqueous compositions can contain one or more water-immiscible oils as a solvent for the active agent.

In the preparation of solid feed compositions, the compounds can be mechanically ground with an innocuous solid such as cereal meal, oyster shell flour, or a solid surface active dispersing agent such as finely divided bentonite or fuller's earth. These compositions can be administered in the form of capsules or tablets or dispersed in an animal feed and such feed used to supply a part or all of the ration. Alternatively, the compounds can be dissolved in an organic solvent such as alcohol or acetone and the resulting mixture dispersed in an animal feed which is then dried to remove the solvent. The compounds can also be dispersed in an edible oil such as coconut, olive, cottonseed or peanut oil and the resulting mixtures dispersed in the feed. These edible oil compositions can contain one of the aforementioned emulsifying materials as a dispersing agent.

In addition to poultry feeds containing a minor amount of the quanidine compound as an effective anticoccidial agent, there are provided in accordance with an additional aspect of this invention poultry feed supplement compositions wherein the heretofore described compound is intimately dispersed in, or admixed with, a suitable nontoxic diluent or carrier. The carrier vehicle employed in these supplement compositions should be one in which the coccidiostat is stable, which is compatible with a finished poultry feed and which can be administered with safety to the animals. These feed supplements, which contain a significantly higher percentage of coccidiostat than does the finished feed, are mixed with or blended into the feedstuff. In order to assure uniform distribution of the coccidiostat in the finished feed, it is customary to employ an intermediate dilution step in which the supplement is blended with a portion of the final feed, and this "intermediate mix" is then added to the remainder of the feed with adequate mixing. The coccidiostat compounds described hereinabove may be formulated into feed supplement compositions containing from about 0.25 percent to about 30 percent by weight of the active ingredient. It will, therefore, be appreciated that the preferred supplement concentration will depend to a large extent on the final use level desired. With the compounds of this invention, feed supplement compositions containing from about 1–20 percent by weight of active ingredient are quite suitable.

The diluents normally employed for these poultry feed supplements are solid orally ingestible poultry feed additives such as distillers' dried grains, corn meal, citrus meal, fermentation residues, ground oyster shells, Attapulgus clay, wheat middling, wheat shorts, molasses solubles, corn cob meal, corn gluten feed, corn germ meal, edible vegetable substances, soybean meal, dehulled soya flour, soybean mill feed, antibiotic mycelia, crushed limestone, soya grits and the like. This dilution serves to facilitate uniform distribution of the substance in the finished feed. The finished feed is one that contains a source of fat, protein, carbohydrate, minerals, vitamins and other nutritional factors.

The following examples will serve to further illustrate this additional feature of the present invention but are not meant to limit it thereto.

EXAMPLE VIII

The hereinafter set forth guanidine compounds were separately dispersed in commercial poultry mash to produce animal feed compositions containing predetermined amounts of one of the guanidine compounds, as the sole active agent. Portions of these compositions were fed, as the sole feed ration, to flocks of chickens of the same history and past environment which were about 17 days old. Other flocks of chickens were fed the same poultry mash, containing none of the guanidine compounds, to serve as controls. One day after the diet was started, 200,000 sporulated *Eimeria necatrix* oocysts and *Eimeria acervulina* oocysts were introduced directly into the crop of the birds. Another flock of chickens was left untreated and uninoculated to serve as an uninfected check. Seven days following the initiation of the diets, the birds were sacrificed, autopsied and an examination made to determine the percent kill and control of coccidiosis and the coccidial organisms. The results of this examination are set forth below in Table I.

TABLE I

| Active Agent Employed in Diet | Amount of active agent in feed in parts by weight per million parts of feed composition | Percent kill and control of mixed culture of *E. necatrix* and *E. acervulina* |
|---|---|---|
| 1,3-Bis[(4-chloro-2-ethoxybenzylidene)amino]-guanidine:hydrochloride | 125 | 40 |
| 1,3-Bis[(4-acetamido-2-ethoxybenzylidene)-amino]guanidine-hydrochloride | 125 | 75 |
| 1,3-Bis[(4-acetamido-2-ethoxybenzylidene)-amino]guanidine | 31 | 74 |
| | 62 | 77 |
| | 125 | 59 |
| 1,2,3-Tris[(4-acetamido-2-ethoxybenzylidene)-amino]guanidine:hydrochloride | 31 | 68 |
| | 62 | 75 |
| | 125 | 79 |
| 1,3-Bis[(4-bromo-2-methoxybenzylidene)amino]-guanidine:hydrobromide | 500 | 92 |
| 1,3-Bis[(4-chloro-2-methoxybenzylidene)amino]-guanidine:hydrobromide in admixture with 1,3-Bis[(5-chloro-2-methoxybenzylidene)-amino]guanidine:hydrobromide | 500 | 81 |
| 1,3-Bis[(3,4-dichloro-2-ethoxybenzylidene)-amino]guanidine:hydrobromide in admixture with 1,3-Bis[(4,5-dichloro-2-ethoxy-benzylidene)amino]guanidine:hydrobromide | 500 | 87 |
| 1,3-Bis[(4-chloro-2-ethoxybenzylidene)-amino]guanidine:hydrobromide in | | |

TABLE I-continued

| Active Agent Employed in Diet | Amount of active agent in feed in parts by weight per million parts of feed composition | Percent kill and control of mixed culture of E. necatrix and E. acervulina |
|---|---|---|
| admixture with 1,3-Bis[(5-chloro-2-ethoxybenzylidene)amino]-guanidine:hydrobromide | 500 | 79 |
| 1,3-Bis[(3,5-dichloro-2-methoxybenzylidene)amino]guanidine:hydrochloride | 250 | 90 |
|  | 500 | 89 |
| 1,3-Bis[(4,5-dichloro-2-methoxybenzylidene)amino]guanidine:hydrochloride | 500 | 63 |
|  | 3000 | 82 |
| 1,3-Bis[(3,5-dibromo-2-methoxybenzylidene)amino]guanidine:hydrochloride | 62 | 51 |
|  | 125 | 79 |
|  | 250 | 88 |
|  | 500 | 86 |
| 1,3-Bis[(4-bromo-2-methoxybenzylidene)-amino]guanidine:hydrochloride | 125 | 100 |
|  | 250 | 100 |
|  | 500 | 100 |
| 1,3-Bis[(3,5-dibromo-2-methoxybenzylidene)amino]guanidine | 500 | 100 |
| 1,3-Bis[(4,5-dichloro-2-ethoxybenzylidene)-amino]guanidine:hydrochloride | 62 | 89 |
|  | 125 | 100 |
|  | 250 | 100 |
|  | 500 | 100 |
| 1,3-Bis[(4,5-dibromo-2-methoxybenzylidene)-amino]guanidine:hydrochloride | 500 | 84 |
| 1,3-Bis[(3,5-dibromo-2-methoxybenzylidene)-amino]guanidine:3-hydroxy-2-naphthalene carboxylic acid | 500 | 100 |
| Infected control | — | 0 |
| Uninfected control | — | 100 |

EXAMPLE IX

The hereinafter set forth guanidine compounds were separately dispersed in commercial poultry mash to produce animal feed compositions containing predetermined amounts of one of the guanidine compounds, as the sole active agent. Portions of these compositions were fed, as the sole feed ration, to flocks of chickens of the same history and past environment which were about 17 days old. Other flocks of chickens were fed the same poultry mash, containing none of the guanidine compounds, to serve as controls. One day after the diet was started, 200,000 sporulated *Eimeria tenella* oocysts were introduced directly into the crop of the birds. Another flock of chickens was left untreated and uninoculated to serve as an uninfected check. Seven days following the initiation of the diets, the birds were sacrificed, autopsied and an examination made to determine the percent kill and control of coccidiosis and the coccidial organisms. The results of this examination are set forth below in Table II.

TABLE II

| Active Agent Employed in Diet | Amount of active agent in feed in parts by weight per million parts of feed composition | Percent kill and control of E. Tenella |
|---|---|---|
| 1,3-Bis[(4-chloro-2-benzyloxybenzylidene)amino]guanidine:hydrochloride | 500 | 72 |
| 1,3-Bis[(4-bromo-2-ethoxybenzylidene)amino]guanidine:hydrochloride | 500 | 96 |
| 1,3-Bis[(4-bromo-2-methoxybenzylidene)amino]guanidine:hydrobromide | 500 | 100 |
| 1,3-Bis[(4-chloro-2-methoxybenzylidene)amino]guanidine:hydrobromide in admixture with 1,3-Bis[(5-chloro-2-methoxybenzylidene)amino]-guanidine:hydrobromide | 500 | 81 |
| 1,3-Bis[(3,4-dichloro-2-ethoxybenzylidene)amino]guanidine:hydrobromide in admixture with 1,3-Bis[(4,5-dichloro-2-ethoxybenzylidene)amino]-guanidine:hydrobromide | 500 | 96 |
| 1,3-Bis[(4-chloro-2-ethoxybenzylidene)-amino]guanidine:hydrobromide in admixture with 1,3-Bis[(5-chloro-2-ethoxybenzylidene)amino]-guanidine:hydrobromide | 500 | 79 |
| 1,3-Bis[(3,5-dichloro-2-methoxybenzylidene)amino]guanidine:hydrochloride | 500 | 100 |
| 1,3-Bis[(4,5-dichloro-2-methoxybenzylidene)amino]guanidine:hydrochloride | 500 | 99 |
| 1,3-Bis[(3,5-dibromo-2-methoxybenzylidene)-amino]guanidine:hydrochloride | 500 | 89 |
| 1,2,3-Tris[(3,5-dichloro-2-methoxybenzylidene)amino]guanidine:hydrochloride | 500 | 49 |
| 1,3-Bis[(4-bromo-2-methoxybenzylidene)-amino]guanidine:hydrochloride | 125 | 100 |
|  | 250 | 97 |
|  | 500 | 100 |

TABLE II-continued

| Active Agent Employed in Diet | Amount of active agent in feed in parts by weight per million parts of feed composition | Percent kill and control of E. Tenella |
|---|---|---|
| 1,3-Bis[(3,5-dibromo-2-methoxybenzylidene)-amino]guanidine | 500 | 85 |
| 1,3-Bis[(4,5-dichloro-2-ethoxybenzylidene)amino]guanidine:hydrochloride | 62 | 69 |
|  | 125 | 100 |
|  | 250 | 100 |
|  | 500 | 100 |
| 1,3-Bis[(3,5-dichloro-2-ethoxybenzylidene)-amino]guanidine:hydrochloride | 500 | 100 |
|  | 250 | 90 |
|  | 125 | 58 |
| 1,3-Bis[(3,5-dibromo-2-methoxybenzylidene)-amino]guanidine:3-hydroxy-2-naphthalene-carboxylic acid | 500 | 78 |
| Infected control | — | 0 |
| Uninfected control | — | 100 |

EXAMPLE X

The hereinafter set forth guanidine compounds were separately dispersed in commercial poultry mash to produce animal feed compositions containing predetermined amounts of one of the guanidine compounds, as the sole active agent. Portions of these compositions were fed, as the sole feed ration, to flocks of chickens of the same history and past environment which were about 17 days old. Other flocks of chickens were fed the same poultry mash, containing none of the guanidine compounds, to serve as controls. One day after the diet was started, 200,000 sporulated *Eimeria necatrix* oocysts were introduced directly into the crop of the birds. Another flock of chickens was left untreated and uninoculated to serve as an uninfected check. Seven days following the initiation of the diets, the birds were sacrificed, autopsied and an examination made to determine the percent kill and control of coccidiosis and the coccidial organisms. The results of this examination are set forth below in Table III.

EXAMPLE XI

The hereinafter set forth guanidine compounds were separately dispersed in commercial poultry mash to produce animal feed compositions containing predetermined amounts of one of the guanidine compounds, as the sole active agent. Portions of these compositions were fed, as the sole feed ration, to flocks of chickens of the same history and past environment which were about 17 days old. Other flocks of chickens were fed the same poultry mash, containing none of the guanidine compounds, to serve as controls. One day after the diet was started, 5,000,000 sporulated *Eimeria acervulina* oocysts were introduced directly into the crop of the birds. Another flock of chickens was left untreated and uninoculated to serve as an uninfected check. Seven days following the initiation of the diets, the birds were sacrificed, autopsied and an examination made to determine the percent kill and control of coccidiosis and the coccidial organism. The results of this examination are set forth below in Table IV.

TABLE III

| Active Agent Employed in Diet | Amount of active agent in feed in parts by weight per million parts of feed composition | Percent kill and control of E. necatrix |
|---|---|---|
| 1,3-Bis[(4-bromo-2-ethoxybenzylidene)-amino]guanidine:hydrochloride | 500 | 96 |
| 1,3-Bis[(4-bromo-2-methoxybenzylidene)-amino]guanidine:hydrobromide | 500 | 88 |
| 1,3-Bis[(3,5-dichloro-2-methoxybenzylidene)-amino]guanidine:hydrochloride | 500 | 68 |
| 1,3-Bis[(4,5-dichloro-2-methoxybenzylidene)-amino]guanidine:hydrochloride | 500 | 48 |
| 1,3-Bis[(4-bromo-2-methoxybenzylidene)-amino]guanidine:hydrochloride | 125 | 100 |
|  | 250 | 97 |
|  | 500 | 100 |
| 1,3-Bis[(3,5-dibromo-2-methoxybenzylidene)-amino]guanidine | 137 | 100 |
|  | 125 | 100 |
|  | 55 | 100 |
| 1,3-Bis[(4,5-dibromo-2-methoxybenzylidene)-amino]guanidine:hydrochloride | 500 | 84 |
| Infected control | — | 0 |
| Uninfected control | — | 100 |

TABLE IV

| Active Agent Employed in Diet | Amount of active agent in feed in parts by weight per million parts of feed composition | Percent kill and control of E. acervulina |
|---|---|---|
| 1,3-Bis[(4-(diethylamino)-2-ethoxybenzylidene)amino]guanidine | 31 | 58 |
|  | 62 | 75 |

TABLE IV-continued

| Active Agent Employed in Diet | Amount of active agent in feed in parts by weight per million parts of feed composition | Percent kill and control of E. acervulina |
|---|---|---|
| | 125 | 75 |
| | 250 | 95 |
| | 500 | 87 |
| 1,3-Bis[(4-acetamido-2-ethoxybenzylidene)-amino]guanidine:hydrochloride | 62 | 60 |
| | 125 | 69 |
| | 250 | 68 |
| | 500 | 77 |
| 1,3-Bis[(4-acetamido-2-ethoxybenzylidene)-amino]guanidine | 31 | 95 |
| | 62 | 77 |
| | 125 | 85 |
| 1,2,3-Tris[(4-acetamido-2-ethoxybenzylidene)-amino]guanidine:hydrochloride | 31 | 77 |
| | 62 | 75 |
| | 125 | 80 |
| | 250 | 77 |
| | 500 | 73 |
| 1,3-Bis[(4-bromo-2-methoxybenzylidene)-amino]guanidine:hydrobromide | 250 | 71 |
| | 500 | 92 |
| 1,2,3-Tris[(4-(diethylamino)-2-ethoxybenzylidene)-amino]guanidine | 31 | 67 |
| | 62 | 79 |
| | 125 | 74 |
| | 250 | 69 |
| | 500 | 66 |
| 1,3-Bis[(4-dimethylamino)-2-ethoxybenzylidene)amino]guanidine | 500 | 74 |
| 1,3-Bis[(3,4-dichloro-2-ethoxybenzylidene)-amino]guanidine:hydrobromide in admixture with 1,3-Bis[(4,5-dichloro-2-ethoxybenzylidene)amino]guanidine:hydrobromide | 500 | 91 |
| 1,3-Bis[(4-amino-2-methoxybenzylidene)-amino]guanidine:hydrochloride | 31 | 70 |
| | 62 | 70 |
| | 125 | 78 |
| | 250 | 60 |
| | 500 | 65 |
| 1,2,3-Tris[(4-amino-2-methoxybenzylidene)-amino]guanidine:hydrochloride | 31 | 70 |
| | 62 | 78 |
| | 125 | 62 |
| | 250 | 69 |
| | 500 | 74 |
| 1,3-Bis[(4-bromo-2-ethoxybenzylidene)-amino]guanidine:hydrochloride | 500 | 85 |
| 1,3-Bis[(3,5-dichloro-2-methoxybenzylidene)amino]guanidine:hydrochloride | 250 | 90 |
| | 500 | 79 |
| 1,3-Bis[(4,5-dichloro-2-methoxybenzylidene)-amino]guanidine:hydrochloride | 500 | 56 |
| 1,3-Bis[(3,5-dibromo-2-methoxybenzylidene)-amino]guanidine:hydrochloride | 125 | 79 |
| | 250 | 95 |
| | 500 | 85 |
| 1,3-Bis[(4-bromo-2-methoxybenzylidene)-amino]guanidine:hydrochloride | 250 | 73 |
| | 500 | 77 |
| 1,3-Bis[(3,5-dibromo-2-methoxybenzylidene)-amino]guanidine | 500 | 100 |
| 1,3-Bis[(4-acetamido-2-methoxybenzylidene)-amino]guanidine:hydrochloride | 31 | 61 |
| | 62 | 69 |
| | 125 | 75 |
| | 250 | 71 |
| | 500 | 88 |
| 1,2,3-Tris[(4-acetamido-2-methoxybenzylidene)amino]guanidine:hydrochloride | 31 | 59 |
| | 62 | 58 |
| | 125 | 65 |
| | 250 | 71 |
| | 500 | 67 |
| 1,3-Bis[(4-amino-2-ethoxybenzylidene)-amino]guanidine:hydrochloride | 31 | 69 |
| | 62 | 92 |
| | 250 | 74 |
| | 500 | 60 |
| 1,2,3-Tris[(4-amino-2-ethoxybenzylidene)-amino]guanidine:hydrochloride | 62 | 85 |
| | 250 | 69 |
| 1,3-Bis[(3,5-dibromo-2-methoxybenzylidene)-amino]guanidine:3-hydroxy-2-naphthalene carboxylic acid | 500 | 100 |
| Infected control | — | 0 |
| Uninfected control | — | 100 |

In a further embodiment, the guanidine compounds as employed in accordance with the present invention, or compositions containing the same, advantageously can be employed in the present methods in combination with one or more other feed additives including agents active against gastrointestinal parasites, as supplemental materials. Representative additives and agents include 2-sulfanilamidoquinoxaline, acetyl(p-nitrophenyl)sulfanilamide, sulfadimethylpyridine, 2,2'-methylene bis(4-chlorophenol), 4,4'-isopropylidene bis(o-cresol), 5-nitro-2-furaldehyde semicarbazone, furoxone N-(5-nitro-2-furfurylidene-3-amino-2-oxazolidone), 3-nitro-4-hydroxyphenyl arsonic acid, p-aminobenzene arsonic acid, (1-(4-amino-2-n-propyl-5-pyrimidinylmethyl)-2-pycolinum chloride hydrochloride), the complex of 4,4'-dinitrocarbanilide and 2- hydroxy-4,6-dimethylpyrimidine, 4,5-imidazole dicarboxamide, methyl-4-acetamido-2-ethoxybenzoate, oxytetracycline, chlorotetracycline, N-(4'-chlorophenyl)-7-oxabicyclo(2.2.1)-heptane-2,3-dicarboxamide, methyl-4-acetamido-2-ethoxybenzoate, tetraethyl thiuram disulfide, arsenosobenzene, 5-nitro-2-furaldehyde acetohydrazone, 2,2'-dihydroxy-3,3', 5,5'-tetrachlorodiphenylsulfide, 4,6-diamino-2,2-dimethyl-1,3,5-triazine hydrochloride, sulfamethazine, sulfamerazine, sulfadimidine, 2,4-diamino-5-(p-chlorophenyl)-6-ethylpyrimidines, 2,4-diamino-5-(3,4-dichlorophenyl)-6,6-diethyl-5,6-dihydro-1,3,5-triazines, 3,5-dinitrobenzamide, 3,5-dinitro-o-toluamide, 2-chloro-4-nitrobenzamide and other analogues 2,4-diamino-5-aryl-6-alkylpyrimidines, 2,4-diamino-5-aryl-6,6-dialkyl-5,6-dihydro-1,3,5-triazines, dinitrobenzamides, dinitrotoluamides and 3,5-dichloro-2,6-dimethylpyridinol.

In representative operations, each of the feed additives identified in the preceding paragraph together with one of the guanidine compounds as shown hereinbefore are mechanically mixed and ground with commercial poultry mash to produce animal feed compositions. In such operations, the materials are employed in amounts sufficient to provide feed compositions containing from about 0.0045 to about 0.0125 percent by weight of one of the feed additives identified in the preceding paragraph and from about 0.006 to about 0.05 percent by weight of one of the guanidine compounds. These compositions are of excellent value in animal husbandry and are adapted to be fed to poultry to obtain maximum normal growth and to mitigate against the attack of protozoan organisms and particularly Eimeria organisms.

Starting Materials

The substituted 2-alkoxybenzaldehydes and the bis- and trisaminoguanidines employed as starting materials are known in the prior art. Those which cannot be obtained commercially can be prepared by the methods taught in the prior art.

What is claimed is:
1. A [(substituted-2-alkoxybenzylidine)amino]-guanidine compound and the pharmacologically acceptable acid addition salts thereof, the guanidine compound corresponding to the formula

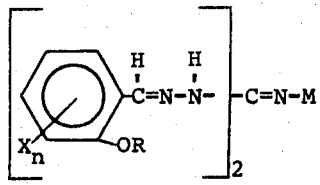

wherein R represents methyl, ethyl or benzyl; X represents chloro, bromo, amino, dimethylamino, diethylamino or acetamido; M represents hydrogen and $n$ represents an integer of 1 or 2 with the proviso that when $n$ is 1, the X representation is in the 4 ring position and when $n$ is 2, the X representations are in any of the 3, 4 or 5 ring positions.

2. The compound as defined in claim 1 which is 1,3-bis[(4-amino-2-ethoxybenzylidene)amino]guanidine.

3. The compound as defined in claim 1 which is 1,3-bis[(4-diethylamino)-2-ethoxybenzylidene)amino]-guanidine.

4. The compound as defined in claim 1 which is 1,3-bis[(4-bromo-2-methoxybenzylidene)amino]-guanidine:hydrobromide.

5. The compound as defined in claim 1 which is 1,3-bis[(3,5-dichloro-2-methoxybenzylidene)amino]-guanidine:hydrochloride.

6. The compound as defined in claim 1 which is 1,3-bis[(3,5-dibromo-2-methoxybenzylidene)amino]-guanidine.

7. The compound as defined in claim 1 which is 1,3-bis[(3,5-dibromo-2-methoxybenzylidene)amino]-guanidine:hydrochloride.

8. A composition comprising from about 5 to 98 percent by weight of a [(substitued-2-alkoxybenzylidene)amino]guanidine compound or a pharmacologically acceptable acid addition salt thereof in intimate admixture with an innocuous carrier therefor, the guanidine compound corresponding to the formula

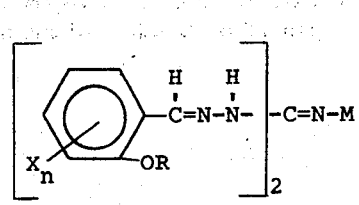

wherein R represents methyl, ethyl or benzyl; X represents chloro, bromo, amino, dimethylamino, diethylamino or acetamido; M represents hydrogen and $n$ represents an integer of 1 or 2 with the proviso that when $n$ is 1, the X representation is in the 4 ring position and when $n$ is 2, the X representations are in any of the 3, 4 or 5 ring positions.

9. A composition containing an animal feed and from about 0.001 to about 0.1 percent by weight of a [(substituted-2-alkoxybenzylidene)amino]guanidine compound or a pharmacologically acceptable acid addition salt thereof, the guanidine compound corresponding to the formula

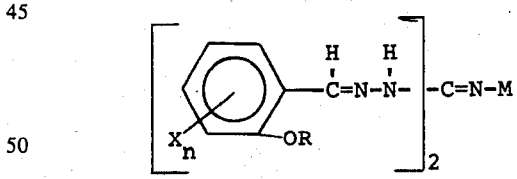

wherein R represents methyl, ethyl or benzyl; X represents chloro, bromo, amino, dimethylamino, diethylamino or acetamido; M represents hydrogen and $n$ represents an integer of 1 or 2 with the proviso that when $n$ is 1, the X representation is in the 4 ring position and when $n$ is 2, the X representations are in any of the 3, 4 or 5 ring positions.

10. In the practice of animal husbandry for protection against coccidiosis, the method which comprises orally administering to animals a [(substituted-2-alkoxybenzylidene)amino]guanidine compound or a pharmacologically acceptable acid addition salt thereof in an amount of from about 3 to about 1,000 parts per million parts of dietary intake, the guanidine compound corresponding to the formula

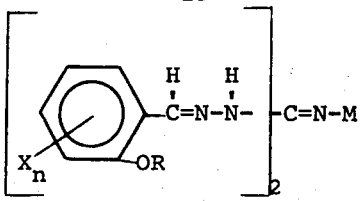

wherein R represents methyl, ethyl or benzyl; X represents chloro, bromo, amino, dimethylamino, diethylamino or acetamido; M represents hydrogen and $n$ represents an integer of 1 or 2 with the proviso that when $n$ is 1, the X representation is in the 4 ring position and when $n$ is 2, the X representations are in any of the 3, 4 or 5 ring positions.

11. The method as defined in claim 10 wherein said guanidine compound or its acid addition salt is in intimate admixture with an innocuous carrier.

12. The method as defined in claim 10 wherein the guanidine compound or its salt is administered in an amount of from about 15 to about 250 parts per million parts of dietary intake.

13. The method as defined in claim 10 wherein the guanidine compound is 1,3-bis[(4-amino-2-ethoxybenzylidene)amino]guanidine.

14. The method as defined in claim 10 wherein the guanidine compound is 1,3-bis[(4-(diethylamino)-2-ethoxybenzylidene)amino]guanidine.

15. The method as defined in claim 10 wherein the guanidine compound is 1,3-bis[(4-bromo-2-methoxybenzylidene)amino]guanidine:hydrobromide.

16. The method as defined in claim 10 wherein the guanidine compound is 1,3-bis[(3,5-dichloro-2-methoxybenzylidene)amino]guanidine:hydrochloride.

17. The method as defined in claim 10 wherein the guanidine compound is 1,3-bis[(3,5-dibromo-2-methoxybenzylidene)amino]guanidine.

18. The method as defined in claim 10 wherein the guanidine compound is 1,3-bis[(3,5-dibromo-2-methoxybenzylidene)amino]guanidine:hydrochloride.

* * * * *